US011555200B2

(12) United States Patent
Roux et al.

(10) Patent No.: US 11,555,200 B2
(45) Date of Patent: Jan. 17, 2023

(54) REGULATION OF COTTON FIBER GROWTH BY EXTRACELLULAR NUCLEOTIDES AND ECTOAPYRASES

(71) Applicant: BOARD OF REGENTS, THE UNIVERSITY OF TEXAS SYSTEM, Austin, TX (US)

(72) Inventors: Stanley J. Roux, Austin, TX (US); Greg Clark, Austin, TX (US); Jonathan Torres, San Antonio, TX (US); Zengjian Jeffrey Chen, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 63 days.

(21) Appl. No.: 16/405,105

(22) Filed: May 7, 2019

(65) Prior Publication Data

US 2020/0087674 A1 Mar. 19, 2020

Related U.S. Application Data

(63) Continuation of application No. 13/132,186, filed as application No. PCT/US2009/066560 on Dec. 3, 2009, now abandoned.

(60) Provisional application No. 61/120,273, filed on Feb. 5, 2008.

(51) Int. Cl.
*C12N 15/82* (2006.01)
*C12N 9/14* (2006.01)

(52) U.S. Cl.
CPC ......... *C12N 15/8261* (2013.01); *C12N 9/14* (2013.01)

(58) Field of Classification Search
None
See application file for complete search history.

(56) References Cited

U.S. PATENT DOCUMENTS

| | | | |
|---|---|---|---|
| 6,448,472 | B1 | 9/2002 | Thomas et al. |
| 2002/0049999 | A1 | 4/2002 | Allen et al. |
| 2002/0077365 | A1 | 6/2002 | Windsor et al. |
| 2002/0103082 | A1 | 8/2002 | Windsor et al. |
| 2002/0173031 | A1 | 11/2002 | Thomas et al. |
| 2003/0008369 | A1 | 1/2003 | Windsor et al. |
| 2008/0058211 | A1 | 3/2008 | Rous |
| 2009/0094717 | A1* | 4/2009 | Troukhan ............ C12Q 1/6895 800/290 |

FOREIGN PATENT DOCUMENTS

| | | |
|---|---|---|
| WO | WO 2005121364 | 12/2005 |
| WO | WO 2010065725 | 6/2010 |

OTHER PUBLICATIONS

Kondou et al. (2009) Plant J 57(5):883-94.*
Klahre et al. (2002) Proc Nat'l Acad Sci 99:11981-86.*
Thomas et al. (2001) Plant J 25:417-25.*
Reynolds et al. (2004) Nature Biotech 22(3):326-30.*
Hanada et al. (2011) Mol Biol Evol 28(1):377-82.*
Kim & Triplett (2001) Plant Physiol 127:1361-66.*
Roux & Steinebruner (2007) Trends Plant Sci 12(11):522-27.*
Wu et al. (2007) Plant Physiol 144:961-75.*
Chivasa et al. (2005) Plant Cell 17:3019-34.*
Cai et al. (2011) Textil Res J 81:239-46.*
Bendtsen, Jannick Dyrlov, et al., Improved Prediction of Signal Peptides—Signal P 3.0, *J. Mol. Biol.*, (2004), 22 pages.
Braun et al., "Sequencing, functional expression and characterization of rat NTPDase6, a nucleoside diphosphatase and novel member of the ecto-nucleoside triphosphate diphosohohydrolase family," *Biochem J.* 351:639-647, 2000.
Wink et al., "Nucleoside Triphosphate Diphosphohydrolase-2 (Ntpdase2/Cd39I1) is the Dominant Ectonucleotidase Expressed by Rat Astrocytes," *Neuroscience* 138:421-432, 2006.
Byeon et al., An increase in melatonin in transgenic rice causes pleiotropic phenotypes, including enhanced seedling growth, delayed flowering, and low grain yield, *J. Pineal Res.* 56:408-414, 2014.
Chen, et al., "Toward Sequencing Cotton (*Gossypium*) Genomes," *Plant Physiology*, Dec. 2007, vol. 145, pp. 1303-1310.
Chen, J. G., et al., "Levels of Cytokinins in the Ovules of Cotton Mutants with Altered Fiber Development", *Journal of Plant Growth Regulation* (1997) 16:181-185.
Clark et al., "Breakthroughs spotlighting roles for extracellular nucleotides and apyrases in stress responses and growth and development," *Plant Science* 225:107-116, 2014.
Clark et al., "Extracellular ATP levels are higher in growth of primary roots of wild-type *Arabidopsis* seedlings and are changed by altered expression of apyrase enzymes and auxin transporters," abstract 600:020, ASPB Plant Biology Meeting, Jun. 2017, Honolulu.
Gendreau et al., "Cellular Basis of Hypocotyl Growth in *Arabidopsis thaliana*," *Plant Physiol.* 114:295-305, 1997.
Gu et al., "Targeting and Regulation of Cell Wall Synthesis During Tip Growth in Plants," *Journal of Integrative Plant Biology* 55(9):835-846, 2013.
Handa et al., "Purification and Cloning of a Soluble ATP-Diphosphohydrolase (Apyrase) from Potato Tubers (*Solanum tuberosum*)," *Biochemical and Biophysical Research Communications* 218:916-923, 1996.
Huang, G., et al., A Fasciclin-Like Arabinogalactan Protein, GhFLA1, Is Involved in Fiber Initiation and Elongation of Cotton1[C][W][OA], *Plant Physiology*, Mar. 2013, vol. 161, pp. 1278-1290.

(Continued)

*Primary Examiner* — Russell T Boggs
(74) *Attorney, Agent, or Firm* — Dentons US LLP

(57) ABSTRACT

The present invention includes compositions and methods of modulating the length of one or more cotton fibers in a plant by contacting the plant or tissue derived therefrom with at least one of: a nucleotide; a modulator of ectoapyrase gene transcription; or an anti-ectoapyrase antibody or fragments thereof, at a concentration that modulates growth of one or more cotton fibers.

3 Claims, 6 Drawing Sheets

Specification includes a Sequence Listing.

(56) References Cited

OTHER PUBLICATIONS

International Search Report and Written Opinion for PCT/US2009/066560, dated Aug. 18, 2010, 14 pages.
Jeter, Collene R., et al., "Evidence of a Novel Cell Signaling Role for Extracellular Adenosine Triphosphates and Diphosphates in *Arabidopsis*," *The Plant Cell*, vol. 16, Oct. 2004, pp. 2652-2664.
Jeter, Collene R., et al., "Plant Responses to Extracellular Nucleotides: Cellular Processes and Biological Effects," *Purinergic Signalling*, (2006), vol. 2, pp. 443-449.
Kim, Hee Jin, et al., "Cotton Fiber Growth in Planta and in Vitro. Models for Plant Cell Elongation and Cell Wall Biogenesis," *Plant Physiology*, Dec. 2001, vol. 127, pp. 1361-1366.
Kim, Sung-Yong, et al., "Extracellular ATP in Plants. Visualization, Localization, and Analysis of Physiological Significance in Growth and Signaling," *Plant Physiology*, Nov. 2006, vol. 142, pp. 984-992.
Knowles, "The GDA1_CD39 superfamily: NTPDases with diverse functions," *Purinergic Signaling* 7:21-45, 2011.
Lee, Jinsuk J., et al., "Gene Expression Changes and Early Events in Cotton Fibre Development," *Annals. of Botany*, (2007), vol. 100, pp. 1391-1401.
Lee, Joohyun, et al., "Xyloglucan endotransglycosylase/hydrolase genes in cotton and their role in fiber elongation", *Planta* (2010) 232:1191-1205 DOI 10.1007/s00425-010-1246-2.
Li, Hong-Bin, et al., "A Cotton Ascorbate Peroxidase is Involved in Hydrogen Peroxide Homeostasis During Fibre Cell Development," *New Phytologist*, (2007), vol. 175, pp. 462-471.
Lim et al., "Apyrase Suppression Raises Extracellular ATP Levels and Induces Gene Expression and Cell Wall Changes Characteristic of Stress Responses," *Plant Physiology* 164:2054-2067, 2014.
Luo, Ming, et al., "GhDET2, a Steriod 5a-Reductase, Plays an Important Role in Cotton Fiber Cell Initiation and Elongation," *The Plant Journal*, (2007), vol. 51, pp. 419-430.
Panikashvili, David, et al., "The *Arabidopsis* Desperado/AtWBC11 Transporter is Required for Cutin and Wax Secreation," *Plant Physiology*, Dec. 2007, vol. 145, pp. 1345-1360.
Pearson, "The Good, the Bad and the Ugly," *Nature* 447:138-140, 2007.
Plesner, "Ecto-ATPases: Identities and Functions," *Int. Rev. Cytol.* 158:141-214, 1995.
Ravnikar, M., et al., "Stimulatory Effects of Jasmonic Acid on Potato Stem Node and Protoplast Culture", *Journal of Plant Growth Regulation* (1992) 11:29-33.
Stiff et al., "Cotton fiber tips have diverse morphologies and show evidence of apical cell wall synthesis," *Scientific Reports* 6:27883, 2016.
Tan, J., et al., "Exogenous Jasmonic Acid Inhibits Cotton Fiber Elongation", Journal Plant *Growth Regulation* (2012) 31:599-605 DOI 10.1007/s00344-012-9260-1.
Tanz et al., "Fluorescent protein tagging as a tool to define the subcellular distribution of proteins in plants," *Frontiers in Plant Science* 4:1-9, 2013.
Tiwari et al., "Cotton (*Gossypium hirsutum*) seed trichomes expand via diffuse growing mechanism," *Can. J. Bot.* 73:746-757, 1995.
Werner, T., et al., "Regulation of plant growth by cytokinin", *PNAS*, Aug. 28, 2001, vol. 98, No. 18, 10489.
Windsor, J.B., et al., "Automated Colorimetric Screen for Apyrase Inhibitors," *BioTechniques*, Nov. 2002, vol. 33, pp. 1024-1030.

Windsor, Brian, et al., "Multiherbicide Tolerance Conferred by AtPgp1 and Apyrase Overexpression in *Arabidopsis Thaliana*," *Nature Biotechnology*, Apr. 2003, vol. 21, pp. 428-433.
Wolf, Carolin, et al., "Developmental Defects and Seedling Lethality in Apyrase AtAPY1 and AtAPY2 Double Knockout Mutants," *Plant Mol. Biol.*, (2007), vol. 64, pp. 657-672.
Yang et al., "Co-regulation of exine wall patterning, pollen fertility and anther dehiscence by Arabidopsis apyrases 6 and 7," *Plant Physiology and Biochemistry* 69:62-73, 2013.
Yegutkin, "Nucleotide- and nucleoside-converting extoenzymes: Important modulators of purinergic signalling cascade," *Biochimica et Biophysica Acta* 1783:673-694, 2008.
Zimmerman, Naunyn Schmiedebergs *Arch Pharmacol* 362:299-309 (2000).
Zhu, Yong-Qing, et al., "An ATP-Binding Cassette Transporter GhWBC1 From Elongating Cotton Fibers," Plant Physiology, Oct. 2003, vol. 133, pp. 580-588.
Navarro-Gochicoa et al., *Plant Physiol* 131:1124-36 (2003).
Wu, Functional analyses of two *Arabidopsis apyrases*. Doctoral Dissertation. p. 1-98. Univ. Texas, Austin (Dec. 2007).
Wu, Jian, et al., "Apyrases (Nucleoside Triphosphate-Diphosphohydrolases) Play a Key Role in Growth Control in *Arabidopsis*," Plant Physiology, Jun. 2007, vol. 144, pp. 961-975.
Roux, Stanley J., et al., "Extracellular ATP: An Unexpected Role as a Signaler in Plants," *Trends in Plant Science*, vol. 12, No. 11, 2007, pp. 522-527.
Chiu et al., *Biochem J* 472:43-54 (2015).
Parsons et al., *Plant Physiol* 159:12-26 (2012).
Steinebrunner et al., *Plant Physiol Biochem* 38:912-22, 914 (2000).
Robson et al., *Purinergic Signal* 2:409-30 (2006).
Crane, *Phil Trans Biol Sci* 359(1444):735-37 (2004).
Govindarajula et al., *Plant Physiol* 149:994-1004 (2009).
Day et al., *MPMI* 13(10) 153-70 (2000).
Zhang, Curr Opin *Plant Biol* 6:430-40 (2003).
Chiu et al., *Plant Cell Physiol* 53:1913-25, 1915 (2012).
Chapman, Numbers Living Species in Australia and the World, 2$^{nd}$ ed. (2009).
Leal et al., Biochim Biophys Acta 1721:9-15 (2005).
He et al., *Plant Cell Physiol.* 46(11):1848-1854 (2005).
Shi, Yong-Hui, et al., "Transcriptome Profiling, Molecular Biological, and Physiological Studies Reveal a Major Role for Ethylene in Cotton Fiber Cell Elongation," *The Plant Cell*, Mar. 2006, vol. 18, pp. 651-664.
Shiller et al., *BMC Plant Biol* 12:123 (2012).
Taliercio, Earl W., et al., "Analysis of Gene Expression in Cotton Fiber Initials," BMC *Plant Biology*, (2007).
Tang, Wenqiang, et al., "Extracellular ATP Inhibits Root Gravitropism at Concentrations that Inhibit Polar Auxin Transport," *Plant Physiology*, Jan. 2003, vol. 131, pp. 147-154.
Thomas, Collin, et al., "Apyrase Functions in Plant Phosphate Nutrition and Mobilizes Phosphate from Extracellular ATP," *Plant Physiology*, Feb. 1999, vol. 119, pp. 543-551.
Massalski et al., *PLOS One* 10:e0115832 (2015).
Stoynova-Bakalova et al., *New Physiol* 62:471-79 (2004).
GenBank, Accession GU365147.1. p. 1-2.
Narasimhulu et al., Early transcription of Agrobacterium T-DNA genes in tobacco and maize. 1996. *Plant Cell*. 8:873-886.

\* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide.

-continued

```
<400> SEQUENCE: 1
atgatcaagc gttcaatggc g                                              21

<210> SEQ ID NO 2
<211> LENGTH: 27
<212> TYPE: DNA
<213> ORGANISM: Artificial Sequence
<220> FEATURE:
<223> OTHER INFORMATION: Synthetic oligonucleotide.

<400> SEQUENCE: 2
cctcattgct gatacagctt cgatggc                                        27

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide.

<400> SEQUENCE: 3
atccacaggc tgctgcaaat                                                20

<210> SEQ ID NO 4
<211> LENGTH: 21
<212> TYPE: DNA
<213> ORGANISM: Artificial Sequence
<220> FEATURE:
<223> OTHER INFORMATION: Syntehtic oligonucleotide.

<400> SEQUENCE: 4
aatgccctca gaccagcagt t                                              21
```

REGULATION OF COTTON FIBER GROWTH BY EXTRACELLULAR NUCLEOTIDES AND ECTOAPYRASES

CROSS-REFERENCE TO RELATED APPLICATIONS

This application is a continuation of U.S. application Ser. No. 13/132,186, filed Aug. 3, 2011, which application is a National Stage Entry of PCT/US2009/066560, filed Dec. 3, 2009, which application claims priority to U.S. Application Ser. No. 61/120,273, filed on Dec. 5, 2008, the contents each of which is incorporated by reference herein in its entirety.

STATEMENT OF FEDERALLY FUNDED RESEARCH

This invention was made with U.S. Government support under Contract No. IOB-0344221 and IOS-0718890 awarded by the NSF. The government has certain rights in this invention.

CROSS-REFERENCE TO RELATED APPLICATIONS

None.

INCORPORATION-BY-REFERENCE OF MATERIALS FILED ON COMPACT DISC

None.

TECHNICAL FIELD OF THE INVENTION

The present invention relates in general to the field of plant fiber growth, and more particularly, to the regulation of plant fiber growth by modulating ectoapyrase activity or gene transcription.

BACKGROUND ART

Without limiting the scope of the invention, its background is described in connection with cotton fiber production. Cotton fibers are some of the longest single cells in the plant kingdom and are considered a model system for studying cell growth and primary cell wall deposition. Upland cotton, *Gossypium hirsutum*, is a widely studied species that has been used for numerous genetic and physiological studies on fiber growth (Wilkins and Arpat, 2005; Shi et al. 2006; Chen et al., 2007; Gao et al. 2007; Lee et al., 2007; Taliercio and Boykin, 2007). Cotton fibers differentiate from the epidermis of the ovule and then undergo cell expansion during the elongation phase of growth from 3 d post-anthesis (dpa) to 16 dpa (Tiwari and Wilkins, 1995; Basra and Malik, 1984) and grow via diffuse growth, which does not share the common ultrastructural characteristics found in tip-growing cells (Tiwari and Wilkins, 1995).

Fiber growth can be conveniently studied in cultured ovules, which allow for testing the effects of various growth regulators on the initiation and elongation processes. For example, Shi et al. (2006) documented the role of ethylene in regulating the growth of cotton fibers in ovule culture, and Qin et al. (2007) showed that very-long-chain fatty acids could promote cotton fiber cell elongation in ovule culture by activating ethylene synthesis.

DISCLOSURE OF THE INVENTION

In one embodiment, the present invention includes compositions and methods of modulating plant fiber growth comprising: contacting a plant cell with one or more extracellular exogenous nucleotides selected from di-nucleotides, tri-nucleotides, or poorly-hydrolyzable nucleotides at a concentration that modulates growth of one or more cotton fibers or cotton fiber cells. In one aspect, the one or more poorly-hydrolyzable nucleotides comprise thio, methylene, amide or methyl-modified ATP, ADP, UTP, UDP, CTP, CDP, TTP, TDP, GTP, GDP, dATP, dADP, dUTP, dUDP, dCTP, dCDP, dTTP, dTDP, dGTP, dGDP, ATPγS, ADPβS, analogues and combinations thereof. In another aspect, the one or more extracellular nucleotides are provided in a concentration that increases growth of the one or more cotton fibers. In another aspect, the one or more extracellular nucleotides are provided in a concentration that decreases growth of the one or more cotton fibers. In another aspect, the one or more extracellular nucleotides are provided at a concentration of between 1 µM and 100 µM to increase the growth of the one or more cotton fibers; between 125 µM and 200 µM to decrease the growth of the one or more cotton fibers; or between 10 µM and 75 µM to increase the growth of the one or more cotton fibers. In yet another aspect, the one or more extracellular nucleotides are provided at a concentration of 5, 10, 20, 30, 40, 50, 60, 70, 80, 90 or 100 µM that increases the growth of the one or more cotton fibers. In another aspect, the one or more extracellular nucleotides are provided at a concentration of 125 µM or greater to decrease the growth of the one or more cotton fibers. In another aspect, the one or more extracellular nucleotides alter the activity of one or more ectoapyrase enzymes by altering the transcription of the ectoapyrase gene(s).

In another embodiment, the present invention includes compositions and methods of modulating plant fiber growth by contacting a plant cell with one or more modulators of ectoapyrase gene transcription, wherein the modulation alters the length of one or more cotton fibers. In one aspect, the one or more modulators of ectoapyrase gene transcription alters ectoapyrase gene transcription are selected from anti-sense or siRNA gene inhibitors. In another aspect, the one or more modulators of ectoapyrase gene transcription are antagonists of ectoapyrase gene transcription to decrease fiber growth. In yet another aspect, the one or more modulators of ectoapyrase gene transcription are agonists of ectoapyrase gene transcription to increase fiber growth.

In another embodiment, the present invention includes a recombinant plant comprising a plant cell that has increased expression of ectoapyrases that increases cotton fiber growth. In another embodiment, the present invention also includes a method of modulating plant fiber growth comprising: contacting a plant cell with one or more inhibitors of ectoapyrase activity comprising an anti-ectoapyrase antibody or fragments thereof, wherein the inhibition decreases the length of one or more cotton fibers.

Yet another embodiment of the present invention includes a composition that modulates the length of one or more cotton fibers in a plant comprising at least one of a poorly-hydrolyzable nucleotide, a modulator of ectoapyrase gene transcription or an anti-ectoapyrase antibody or fragments thereof, at a concentration that modulates growth of one or more cotton fibers. In one aspect, the one or more poorly-hydrolyzable nucleotides comprise thio, methylene, amide or methyl-modified ATP, ADP, UTP, UDP, CTP, CDP, TTP, TDP, GTP, GDP, dATP, dADP, dUTP, dUDP, dCTP, dCDP, dTTP, dTDP, dGTP, dGDP, ATPγS, ADPβS, analogues and combinations thereof. In another aspect, the one or more extracellular nucleotides are provided in a concentration that increases growth of the one or more cotton fibers.

For example, the one or more extracellular nucleotides are provided in a concentration that decreases growth of the one or more cotton fibers. In another aspect, the one or more extracellular nucleotides are provided at a concentration of between 1 µM and 100 µM to increase the growth of the one or more cotton fibers; between 125 µM and 200 µM to decrease the growth of the one or more cotton fibers; or between 10 µM and 75 µM to increase the growth of the one or more cotton fibers. In yet another aspect, the one or more extracellular nucleotides are provided at a concentration of 5, 10, 20, 30, 40, 50, 60, 70, 80, 90 or 100 µM that increases the growth of the one or more cotton fibers. In another aspect, the one or more extracellular nucleotides are provided at a concentration of 125 µM or greater to decrease the growth of the one or more cotton fibers. In another aspect, the one or more extracellular nucleotides alter the activity of one or more ectoapyrase enzymes.

Yet another embodiment of the present invention is a recombinant plant exhibiting increased cotton fiber growth as compared to the corresponding wild-type plant, wherein the recombinant plant comprises a recombinant nucleic acid encoding an ectoapyrase gene inhibitor operably associated with a regulatory sequence. In one aspect, the regulatory sequence is a promoter, a constitutive promoter or an inducible promoter. In another aspect, the nucleic acid is contained within a T-DNA derived vector. In another embodiment, the recombinant plant tissue is derived from the recombinant plant exhibiting increased cotton fiber growth. In another embodiment, the invention is a recombinant seed is derived from the recombinant plant exhibiting increased cotton fiber growth.

Yet another embodiment of the present invention is a method of making a recombinant plant exhibiting increased cotton fiber growth as compared to the corresponding wild-type plant comprising: contacting plant cells with a nucleic acid encoding an inhibitor of an ectoapyrase, wherein the nucleic acid is operably associated with a regulatory sequence to obtain transformed plant cells; producing plants from the transformed plant cells; and selecting a plant exhibiting the increased cotton fiber growth and yield. In one embodiment, the recombinant plant tissue is derived from the recombinant plant exhibiting increased cotton fiber growth. In another aspect, the recombinant seed is derived from the recombinant plant exhibiting increased cotton fiber growth.

DESCRIPTION OF THE DRAWINGS

For a more complete understanding of the features and advantages of the present invention, reference is now made to the detailed description of the invention along with the accompanying figures and in which.

DESCRIPTION OF THE INVENTION

Figure 1A:
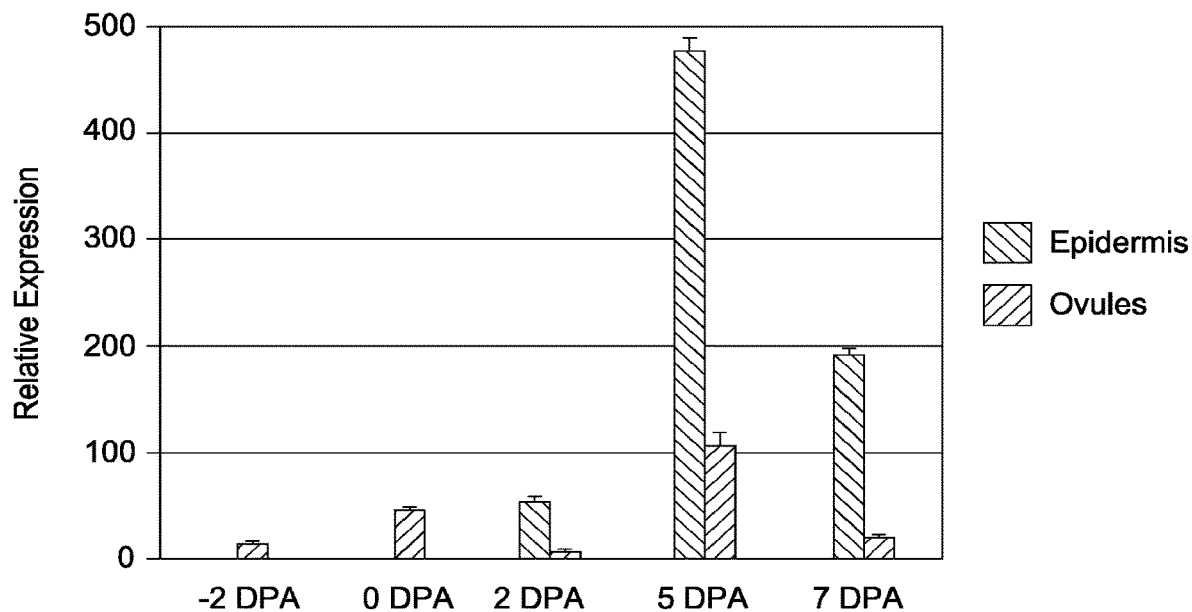
FIG. 1. GhAPY1 is expressed in cotton fibers during elongation phase of growth. [A] Quantitative RT-PCR analysis of GhAPY1 expression shows that expression of this apyrase is fiber specific and is rapidly up-regulated during in vitro fiber growth. [B] Immunoblot analysis using anti-apyrase APY1 and APY2 antibodies confirms that there is an immunodectable apyrase in growing cotton fibers.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Ectoapyrases (NTPDases) are enzymes that remove the terminal phosphate from extracellular nucleoside tri- and diphosphates. In Arabidopsis, two ectoapyrases, AtAPY1 and AtAPY2, have been implicated as key modulators of growth based on genetic and inhibitor studies and on the expression patterns of their genes. Fibers of cotton (*Gossypium hirsutum*) strongly express an apyrase, GhAPY1, whose amino acid sequence closely resembles the two Arabidopsis ectoapyrases. Message and protein levels for GhAPY1 are upregulated when fibers enter their rapid growth phase. In an ovule culture system, fibers release ATP as they grow, and when their apyrase activity is blocked by the addition of polyclonal anti-apyrase antibodies or by small molecule inhibitors, the medium ATP level rises and fiber growth is suppressed. High concentrations of the poorly hydrolysable nucleotides ATPγS and ADPβS applied to the medium inhibit fiber growth, and low concentrations of them stimulate growth. Treatment of cotton ovule cultures with AMPS causes no change in the growth rate of cotton fibers. Both the inhibition and stimulation of growth can be blocked by PPADS and RB2, two antagonists that block purinoceptors in animal cells, and by the feedback inhibitor, adenosine. These data indicate that ectoapyrases and extracellular nucleotides play a significant role in regulating cotton fiber growth.

Ectoapyrases (ecto-NTPDases) are well characterized in animal cells, where they play a key role in reducing the concentration of extracellular nucleotides (e.g., eATP and eADP), which function as signaling agents to activate purinoceptors and induce diverse physiological responses, ranging from neurotransmission to programmed cell death (Burnstock, 2008; Zebisch and Strater, 2008). In Arabidopsis, two ectoapyrase enzymes, AtAPY1 and AtAPY2, play a critical role in controlling the growth of all Arabidopsis tissues tested thus far (Wu et al., 2007). More recently Riewe et al. (2008) showed that apyrases could regulate potato tuber growth. In Arabidopsis, these enzymes are most strongly expressed in rapidly growing tissues, such as etiolated hypocotyls, pollen tubes, and the elongation zone of roots (Wu et al., 2007).

Kim et al. (2006) used a recombinant hybrid reporter protein (luciferase with a cellulose binding domain attached) to visualize ATP in the ECM of plant cells and observed that the highest levels of ATP are found outside of actively growing plant cells like root hairs. These results suggest that plant cells, like animal cells, release ATP into the extracellular matrix (ECM) via fusion of secretory vesicles to the plasma membrane during the growth of plant cells.

Extracellular ATP and the ectoapyrases that limit its concentration can regulate growth and diverse other responses in plants (Roux and Steinebrunner, 2007). These findings led us to hypothesize that ectoapyrase activity might influence the growth of cotton fibers. In this study it was found that the expression of the cotton apyrase that most resembles AtAPY1 and AtAPY2 is highest during the rapid growth phase of the fibers, and that inhibition of apyrase activity by the addition of chemical apyrase inhibitors or anti-APY1/APY2 Arabidopsis antibodies to cotton ovule cultures can inhibit cotton fiber growth. Moreover, applied nucleotides can promote or inhibit cotton fiber growth in a dose-dependent manner, and these effects are blocked by the same antagonists of purinoceptors that block the effects of extracellular nucleotides in animals. Taken together, our results support the novel conclusion that extracellular nucleotides and ectoapyrases play an important regulatory role during cotton fiber growth.

As used herein, the phrase "transgenic DNA construct" refers to a segment of DNA that is introduced into the genome of a parental cotton line of plant. While a transgenic DNA construct can comprise any segment of DNA that is heterologous to the insertion site, in preferred aspects of the invention the transgenic DNA construct will be designed to provide a specific function, e.g., suppress or over express an ectoapyrase protein. Useful transgenic DNA constructs may include gene regulatory segment operably linked to the protein coding segment or antisense segments. Non-limiting examples of gene regulatory segment include: promoter elements, enhancers, silencers, introns and untranslated regions.

As used herein, the term "transformation" refers to a method of introducing a transgenic DNA construct into a plant genome and can include any of the well-known and demonstrated methods including: electroporation (e.g., U.S. Pat. No. 5,384,253); microprojectile bombardment (e.g., U.S. Pat. Nos. 5,015,580; 5,550,318; 5,538,880; 6,160,208; 6,399,861 and 6,403,865); *Agrobacterium* mediated transformation (e.g., U.S. Pat. Nos. 5,635,055; 5,824,877; 5,591,616; 5,981,840 and 6,384,301); and protoplast transformation (e.g., U.S. Pat. No. 5,508,184), relevant portions of each are incorporated herein by reference.

As used herein, the term "tissue from a parental cotton line" refers to tissue that is specifically adapted for a selected method of transformation and can include cell culture or embryonic callus.

Nucleic acid molecules of the present invention may be used in transformation, e.g., integrating exogenous genetic material into a plant cell and the plant cell regenerated into a whole plant. As used herein, an "exogenous coding region" or "selected coding region" refers to a coding region not normally found in the host genome in an identical context. By "exogenous coding region", it is meant that the coding region may be isolated from a different species than that of the host genome, or alternatively, isolated from the host genome, but is operably linked to one or more regulatory regions which differ from those found in the unaltered, native gene. An exogenous nucleic acid molecule can have a naturally occurring or non-naturally occurring nucleotide sequence. One skilled in the art understands that an exogenous nucleic acid molecule can be a nucleic acid molecule derived from a different or the same species into which it is introduced. Such exogenous genetic material may be transferred into either monocotyledons and dicotyledons including but not limited to the plants, soy, cotton, canola, maize, wheat and rice.

Exogenous genetic material that increase or decrease the expression of ectoapyrases in plants may be transferred into a plant cell by the use of a DNA vector or construct designed for such a purpose. Vectors have been engineered for transformation of constructs comprising one or more nucleic acid molecules into plant genomes. Vectors have been designed to replicate in both *E. coli* and *A. tumefaciens* and have all of the features required for transferring large inserts of DNA into plant chromosomes. Exogenous genetic material may be transferred into a host cell by the use of a DNA vector or construct designed for such a purpose.

To suppress ectoapyrase protein gene expression, the heterologous DNA can be designed to produce a gene silencing effect, e.g., by an antisense or RNAi mechanism. Anti-sense suppression of genes in plants by introducing by transformation of a construct comprising DNA of the gene of interest in an anti-sense orientation is disclosed in U.S. Pat. Nos. 5,107,065; 5,453,566; 5,759,829; 5,874,269; 5,922,602; 5,973,226; 6,005,167; relevant portion of all of which are incorporated herein by reference. Interfering RNA suppression of genes in a plant by introducing by transformation of a construct that includes DNA encoding a small (commonly less than 30 base pairs) double-stranded piece of RNA matching the RNA encoded by the gene of interest is disclosed in U.S. Pat. Nos. 5,190,931; 5,272,065; 5,268,149, relevant portion of which are incorporated herein by reference.

Vectors that may be used for plant transformation may include, for example, Geminiviruses, plasmids, cosmids, YACs (yeast artificial chromosomes), BACs (bacterial artificial chromosomes), PACs (plant artificial chromosomes), or any other suitable cloning system. A variety of plant viruses that can be employed as vectors are known in the art and include cauliflower mosaic virus (CaMV), geminivirus, brome mosaic virus, and tobacco mosaic virus. Particularly useful for transformation are expression cassettes which have been isolated from such vectors. DNA segments used for transforming plant cells will, of course, generally comprise the cDNA, gene or genes which one desires to introduced into and have expressed in the host cells. These DNA segments can further include structures such as promoters, enhancers, 3' untranslated regions (such as polyadenylation sites), polylinkers, or even regulatory genes as desired.

Examples of plant viruses suitable for delivery of the ectoapyrase modulators of the present invention include, e.g., wheat dwarf virus, maize streak virus, tobacco yellow dwarf virus, tomato golden mosaic virus, abutilon mosaic virus, cassava mosaic virus, beet curly top virus, bean dwarf mosaic virus, bean golden mosaic virus, chloris striate mosaic virus, digitaria streak virus, miscanthus streak virus, maize streak virus, panicum streak virus, potato yellow mosaic virus, squash leaf curl virus, sugarcane streak virus, tomato golden mosaic virus, tomato leaf curl virus, tomato mottle virus, tobacco yellow dwarf virus, tomato yellow leaf curl virus, African cassava mosaic virus, and the bean yellow dwarf virus.

A number of promoters that are active in plant cells have been described in the literature. Such promoters would include but are not limited to: nopaline synthase (NOS) and octopine synthase (OCS) promoters that are carried on tumor-inducing plasmids of *Agrobacterium tumefaciens*, the caulimovirus promoters such as the cauliflower mosaic virus (CaMV) 19S and 35S promoters and the figwort mosaic virus (FMV) 35S promoter, the enhanced CaMV35S promoter (c35S), the light-inducible promoter from the small subunit of ribulose bisphosphate carboxylase (ssRUBISCO, a very abundant plant polypeptide). All of these promoters have been used to create various types of DNA constructs that have been expressed in plants. See, for example PCT publication WO 84/02913, relevant portions incorporated herein by reference.

Once the appropriate plant cells are produced that includes the ectoapyrase gene modulator, the nucleotide sequences of interest can be introduced into the plant cells by any method known in the art to obtain genetically modified plants, plant cells, plant tissue, and seed. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection, electroporation, *Agrobacterium*-mediated transformation, direct gene transfer, and ballistic particle acceleration.

Various types of plant tissue can be used for transformation such as embryo cells, meristematic cells, leaf cells, or callus cells derived from embryo, leaf or meristematic cells, however, any transformation-competent cell or tissue can be used. Various methods for increasing transformation frequency are disclosed in WO 99/61619; WO 00/17364; WO 00/28058; WO 00/37645; U.S. Ser. No. 09/496,444; WO 00/50614; US 01/44038; and WO 02/04649, relevant portions incorporated herein by reference. Once the DNA sequence of interest has been introduced into tissue from the plant, transformed cells are selected and transgenic plants regenerated using methods well known in the art.

Transformed plant cells that are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker that has been introduced together with a polynucleotide of the present invention. For transformation and regeneration of plants (e.g., maize) typically produces shoots within two to four weeks and these transformed shoots are then transferred to an appropriate root-inducing medium containing the selective agent and an antibiotic to prevent bacterial growth. Regeneration can also be obtained from plant callus, explants, organs, or parts thereof. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988), relevant portions incorporated herein by reference.

Certain vectors may be constructed and employed to specifically target the ectoapyrase gene modulation construct within the cells of a transgenic plant or in directing a protein to the extracellular environment. Specific targeting can be accomplished by joining a DNA sequence encoding a transit or signal peptide sequence to the coding sequence of a particular gene. An intracellular targeting DNA sequence may be operably linked 5' or 3' to the coding sequence depending on the particular targeting sequence, e.g., a signal peptide that transports the protein to a particular intracellular, or extracellular destination, respectively, and will then be post-translationally removed.

During selection, several antibiotic resistance markers may be used to select (positively or negatively) the constructs that over or under express ectoapyrases for use with the present invention, including genes that confer resistance to: kanamycin (nptII), hygromycin B (aph IV) and gentamycin (aac3 and aacC4) as well as herbicides such as glufosinate (bar orpat) and glyphosate (EPSPS).

Characterization of cotton apyrase (GhAPY1). The deduced amino acid sequence of GhAPY1 is 471 amino acids in length and possesses all four of the characteristic apyrase conserved regions. An alignment of the deduced amino acid sequence of the coding regions of GhAPY1, AtAPY1 and AtAPY2 shows significant sequence similarity with GhAPY1 and AtAPY1 sharing 67% identity and GhAPY1 and AtAPY2 sharing 68% identity. Within the apyrase conserved regions, however, GhAPY1 and AtAPY1 share 97.5% identity, while GhAPY1 and AtAPY2 share 92.5% identity. A query of the predicted full cotton apyrase amino acid sequence using the SignalP 3.0 Server suggests a high probability that there is an uncleavable signal peptide between residues 20 and 40 (Bendtsen et al., 2004).

Figure 1B:
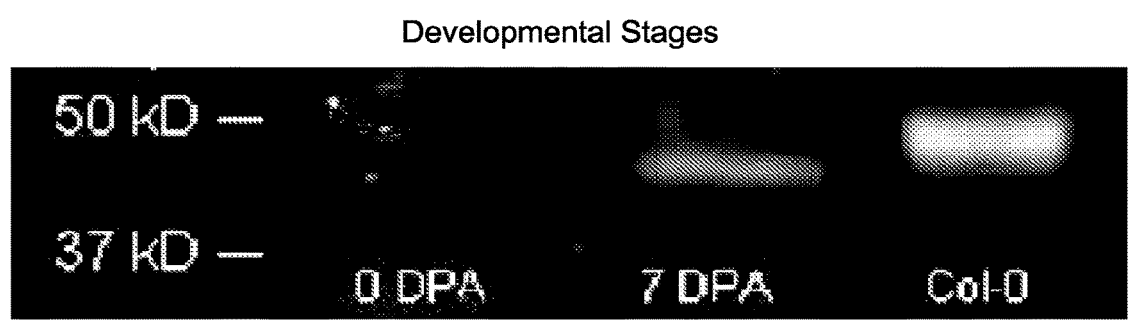

Expression of GhAPY1 correlates with rapid phase of fiber elongation. Quantitative RT-PCR analysis of epidermis (fiber) and ovules tissue over a time course during early fiber growth and development shows that GhAPY1 transcript is mainly found in growing cotton fibers (FIG. 1A). GhAPY1 message first appears in fibers at 2 dpa and then levels dramatically increase showing a peak at 5 dpa. At 7 dpa message levels are lower than at 5 dpa but there is still substantial GhAPY1 expression at this time point. Immunoblot analysis using anti-APY1 and APY2 antibodies shows that there is a cross-reactive protein in 7 dpa fiber samples with a similar molecular weight as the Arabidopsis apyrase (FIG. 1B).

Figure 2A:
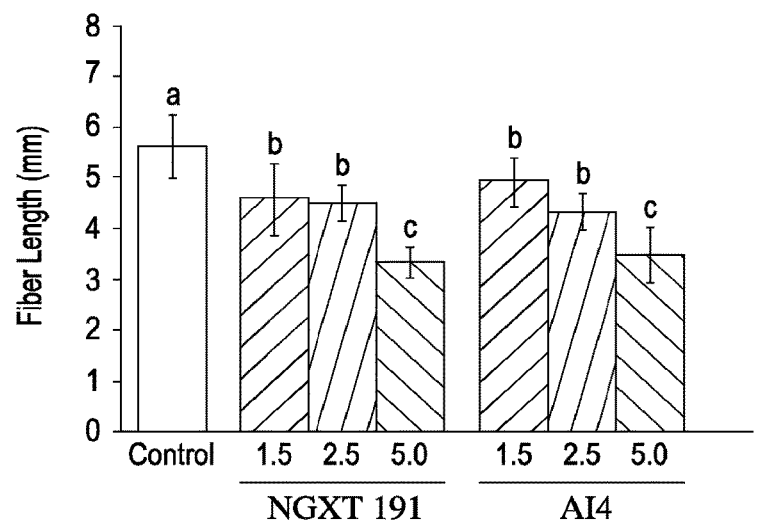
FIG. 2. Inhibition of apyrase activity in cotton ovule cultures using chemical inhibitors decreases overall fiber growth and increases eATP levels. [A] Treatment of cotton ovule cultures with varying concentrations (µg/mL) apyrase inhibitors NGXT 191 and apyrase inhibitor 4 at 3 dpa and 5 dpa decreases average fiber lengths at 7 dpa. [B] Inhibition of fiber growth induced by application of apyrase inhibitors NGXT 191 and apyrase inhibitor 4 (5 µg/mL) at 3 dpa and 5 dpa is reversed by co-incubation with 250 µM PPADS. [C] Treatment of cotton ovule cultures with varying concentrations (µg/mL) apyrase inhibitors NGXT 191 and apyrase inhibitor 4 at 3 dpa and 5 dpa increases the amount of ATP surrounding the cotton fibers. Different letters above the bars indicate mean values that are significantly different from one another ($p<0.05$; $n \geq 24$).
Figure 2B:
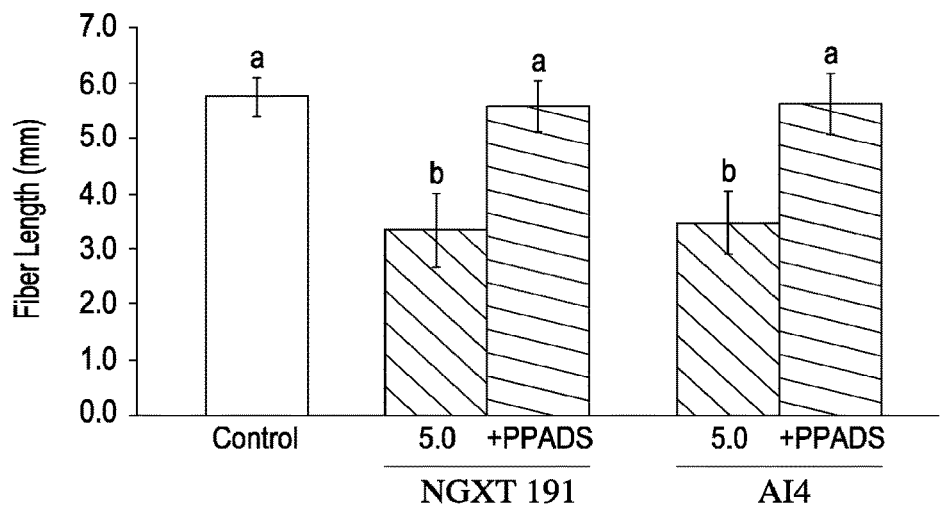
Figure 2C:
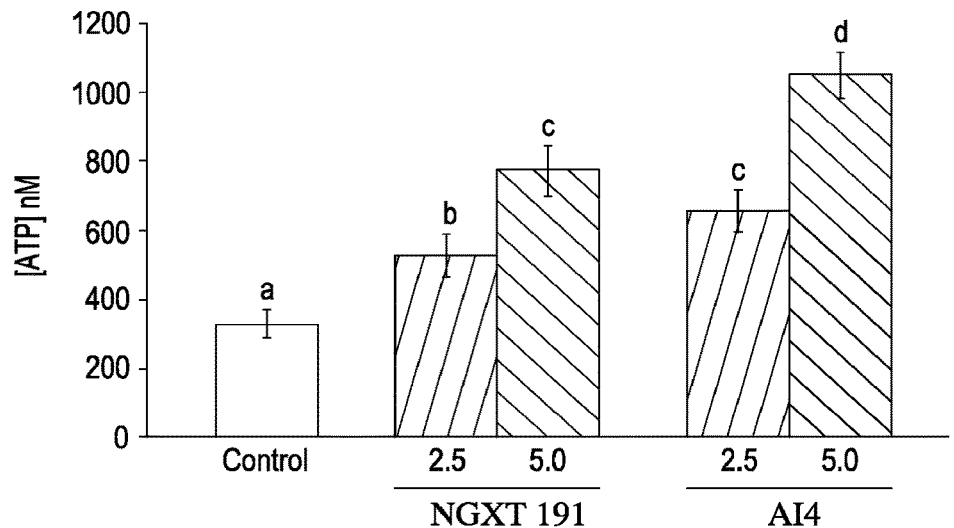

Apyrase inhibitors and anti-apyrase antibodies inhibit fiber elongation. In order to test whether apyrase activity is important during cotton fiber growth we applied varying concentrations of two different chemical apyrase inhibitors, apyrase inhibitor 4 and NGXT191, to cotton ovule cultures at 3 dpa and 5 dpa. It was found that application of all three concentrations of both inhibitors resulted in statistically significant inhibition of fiber growth when cotton fibers were measured at 7 dpa (FIG. 2A). There is clearly a dose-dependent effect, and the effects at each dosage are statistically significant. Apyrase inhibitor treatments also resulted in statistically significant inhibition of cotton fiber growth when fiber lengths were measured at 5 dpa and 19 dpa (data not shown). The level of inhibition increased with increasing concentrations of both inhibitors. Next when PPADS, an inhibitor of animal purinoceptors, was tested, it could block the 40% inhibition of fiber growth caused by application of the highest concentration of apyrase inhibitors. Growth was returned to control levels when 250 µM PPADS was included in the media (FIG. 2B). In order to determine if the observed growth effects were indeed due to inhibition of apyrase activity we measured the amount of ATP found in the media outside of the fibers and found that indeed the inhibitor treatments increased the amount of detectable ATP outside of the growing fibers from the control level of 330 nM (FIG. 2C). As expected increasing the amount of the inhibitor used resulted in higher levels of ATP measured outside of the growing fibers. Application of the highest concentration of inhibitors NGXT191 and 4 caused a 2.1-fold and 3.2-fold increase in ATP levels, respectively.

Figure 3A:
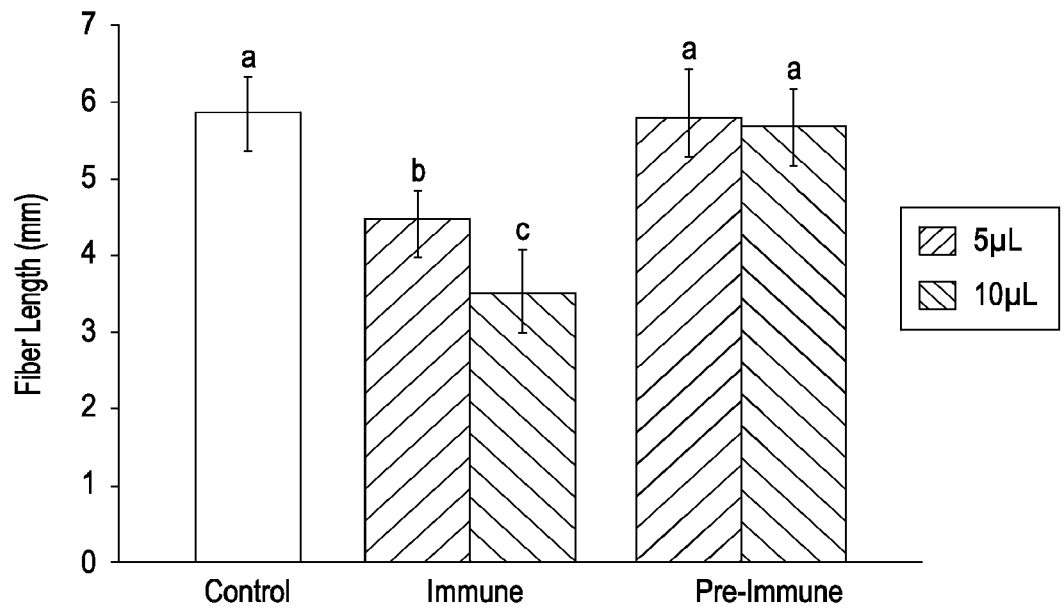
FIG. 3. Inhibition of apyrase activity in cotton ovule cultures using apyrase antibodies decreases overall fiber growth and increases eATP levels. [A] Treatment of cotton ovule cultures with polyclonal anti-apyrase antibodies at 3 dpa and 5 dpa decreases average fiber lengths at 7 dpa. The difference in growth of fibers treated with pre-immune serum was not statistically different ($p>0.05$; $n \geq 24$); the difference in average fiber lengths treated with immune serum and of tubes treated with buffer is statistically significant ($p<10^{-9}$; n in every case$\geq 20$). The protein concentration of the pre-immune sera was 0.3 µg/µL, and of the immune sera was 0.4 µg/µL. [B] Treatment of cotton ovule cultures with polyclonal anti-apyrase antibodies at 3 dpa and 5 dpa increases the amount of ATP surrounding the cotton fibers. Different letters above the bars indicate mean values that are significantly different from one another ($p<0.05$; $n \geq 24$).
Figure 3B:
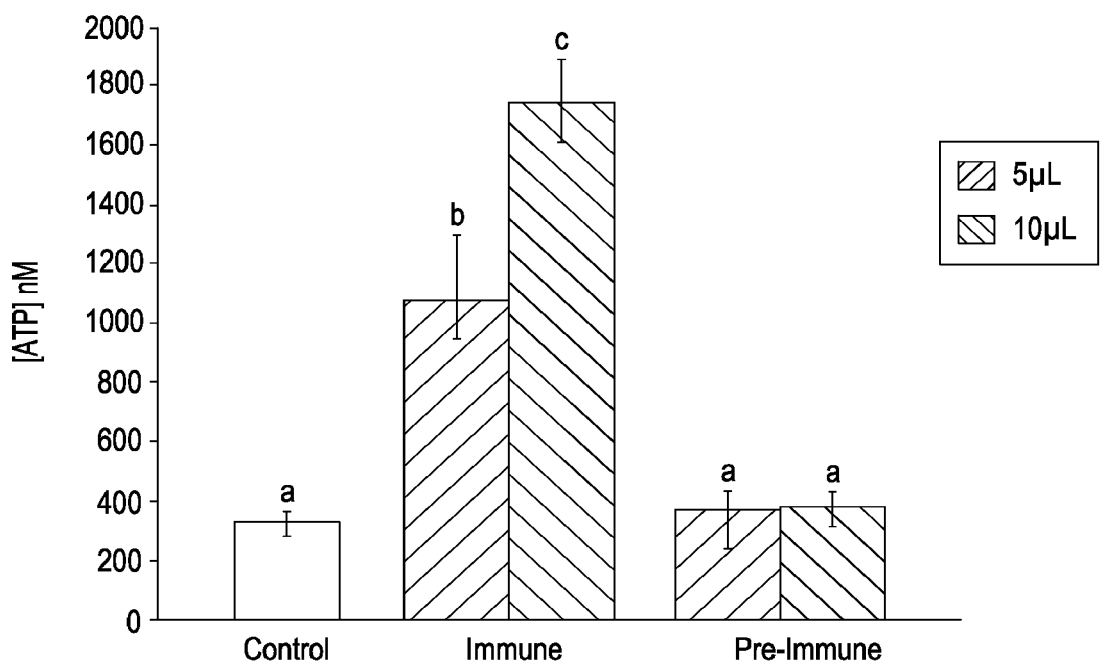

Next, the effects of applying to the cotton ovule cultures polyclonal antibodies raised against Arabidopsis APY1 and APY2 were tested and demonstrated inhibition of apyrase activity (Wu et al., 2007). It was found that treatment with immune sera led to statistically significant inhibition of fiber growth while pre-immune sera had no effect on growth (FIG. 3A). It was also observed that a 3.3 fold and 5.3-fold increase in the level of ATP in the culture medium was detectable after application of the lower and higher antibody concentrations, respectively (FIG. 3B).

Figure 4A:
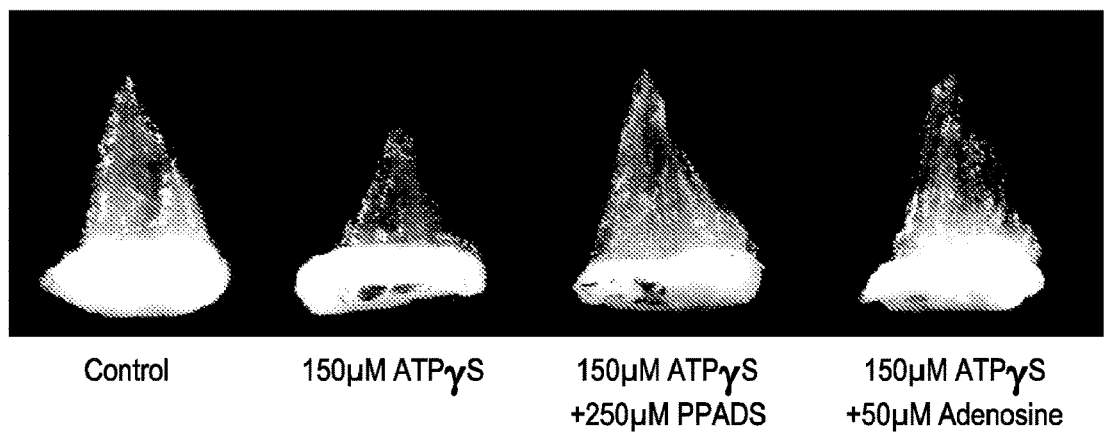
FIG. 4. High concentrations of ATPγS and ADPβS decrease overall cotton fiber growth. [A] Representative image of effects of application of 150 µM ATPγS or 150 µM ATPγS+250 µM PPADS on cotton fiber growth. [B] Application of 150 µM ATPγS and ADPβS to cotton ovule cultures. Different letters above the bars indicate mean values that are significantly different from one another ($p<0.05$; $n \geq 24$).
Figure 4B:
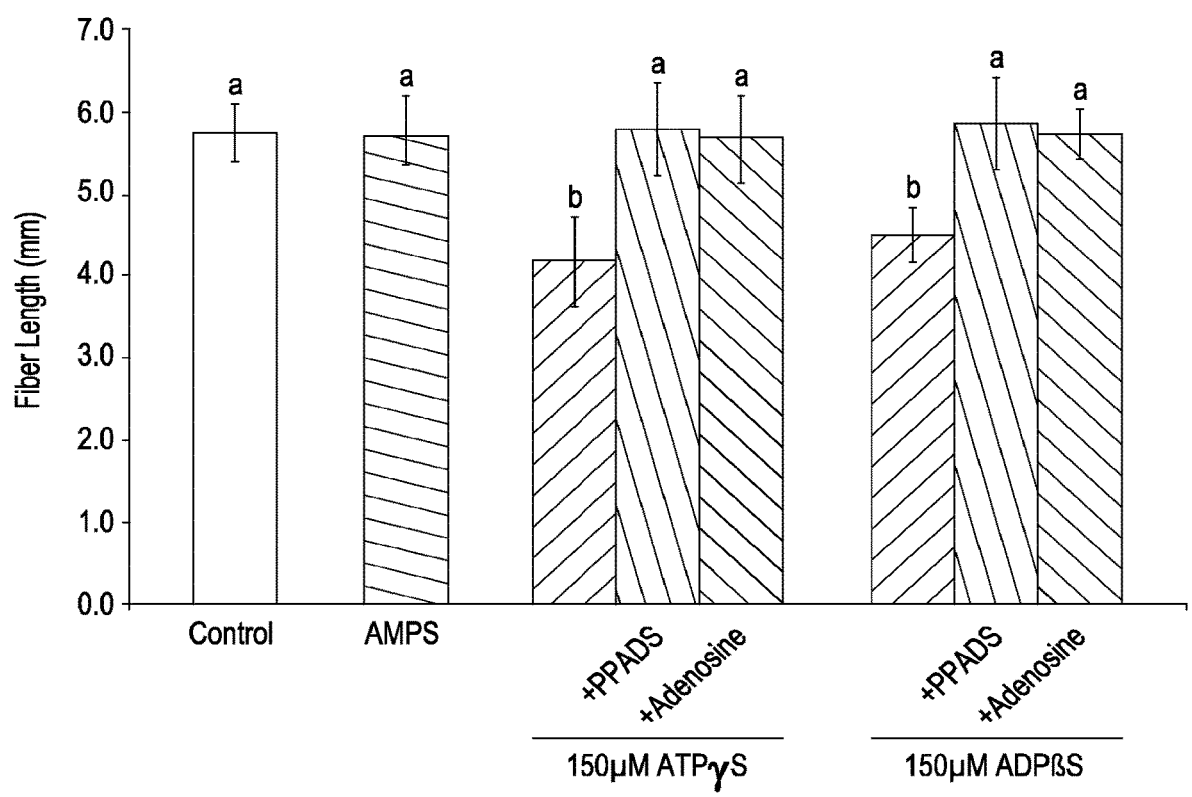

Application of high levels of ATPγS and ADPβS inhibit fiber elongation. The results from the inhibitor and antibody treatments suggest that accumulation of ATP in the fiber ECM causes inhibition of fiber elongation. In order to directly test this hypothesis, we applied poorly hydrolysable nucleotides to ovule cell cultures. It was found that at 7 dpa application of 150 µM ATPγS and ADPβS did indeed inhibit growth and that application of 200 µM AMPS, a closely related molecule but not a purinoceptor agonist, had no effect on growth (FIG. 4A, B). Statistically significant levels of inhibition of cotton fiber growth at 5 dpa by application of high concentrations of 150 µM ATPγS were found. Furthermore, the effects of these high concentrations of ATPγS and ADPβS were reversed by inclusion of PPADS and Adenosine, two known purinoceptor antagonists.

Figure 5A:
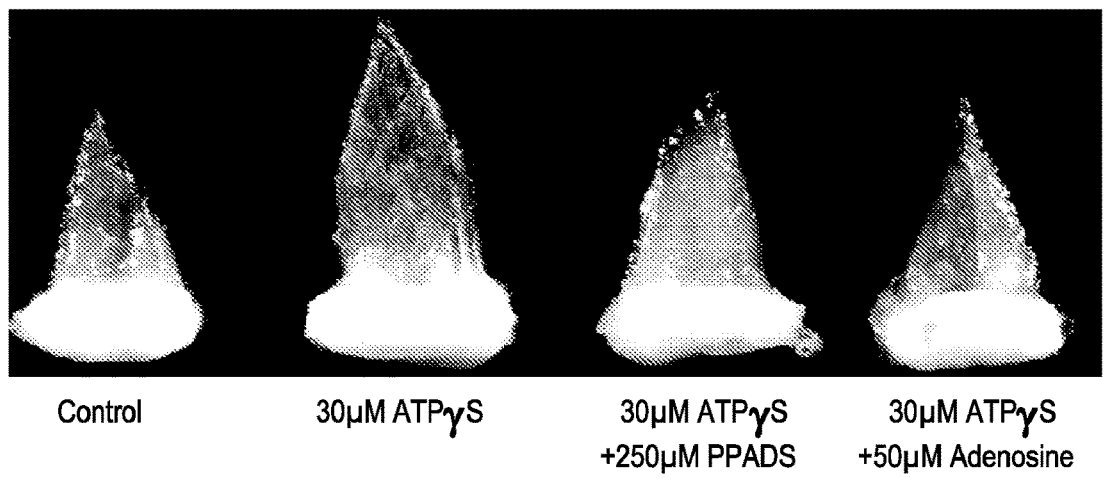
FIG. 5. Low concentrations of ATPγS and ADPβS increases overall cotton fiber growth. [A] Representative image of effects of application of 30 µM ATPγS or 30 µM ATPγS+250 µM PPADS on cotton fiber growth. [B] Application of 30 µM ATPγS or ADPβS to cotton ovule cultures. Different letters above the bars indicate mean values that are significantly different from one another ($p<0.05$; $n \geq 24$).
Figure 5B:
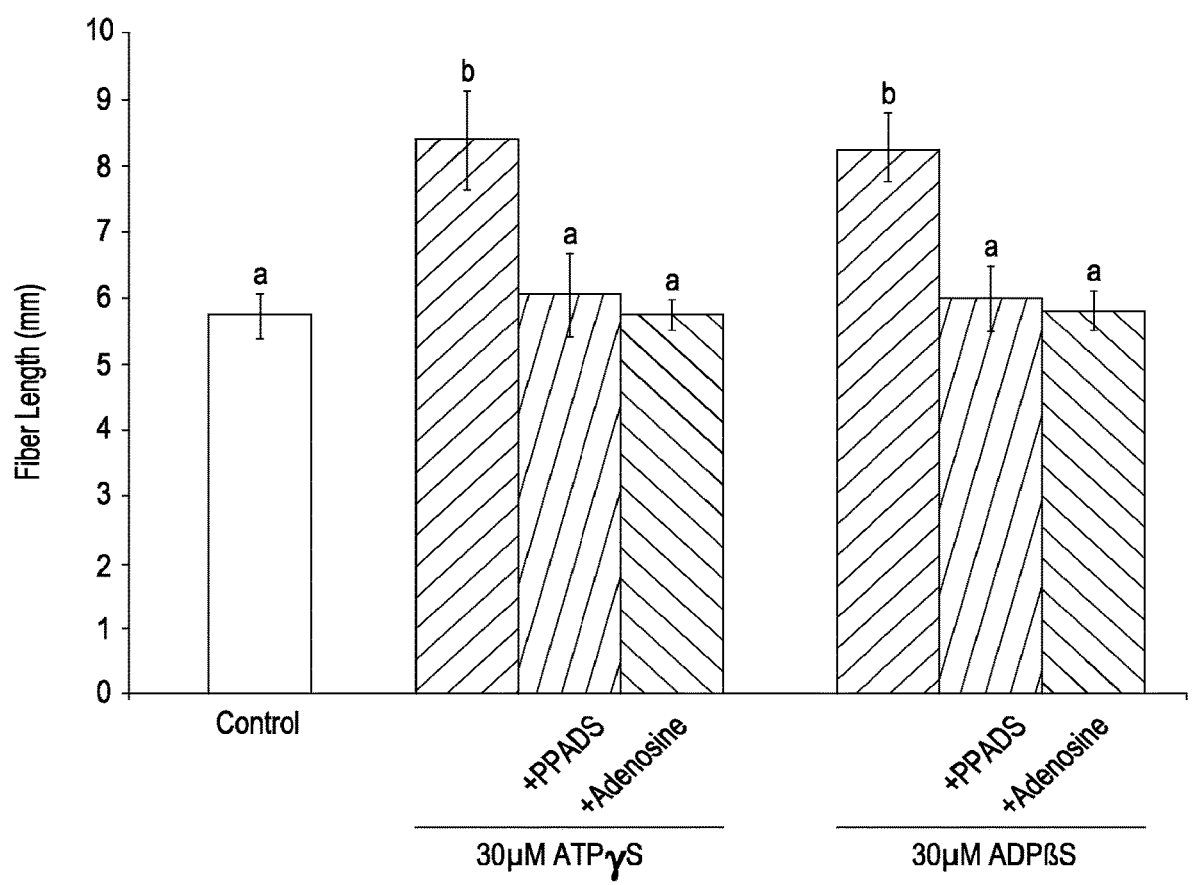
Figure 6:
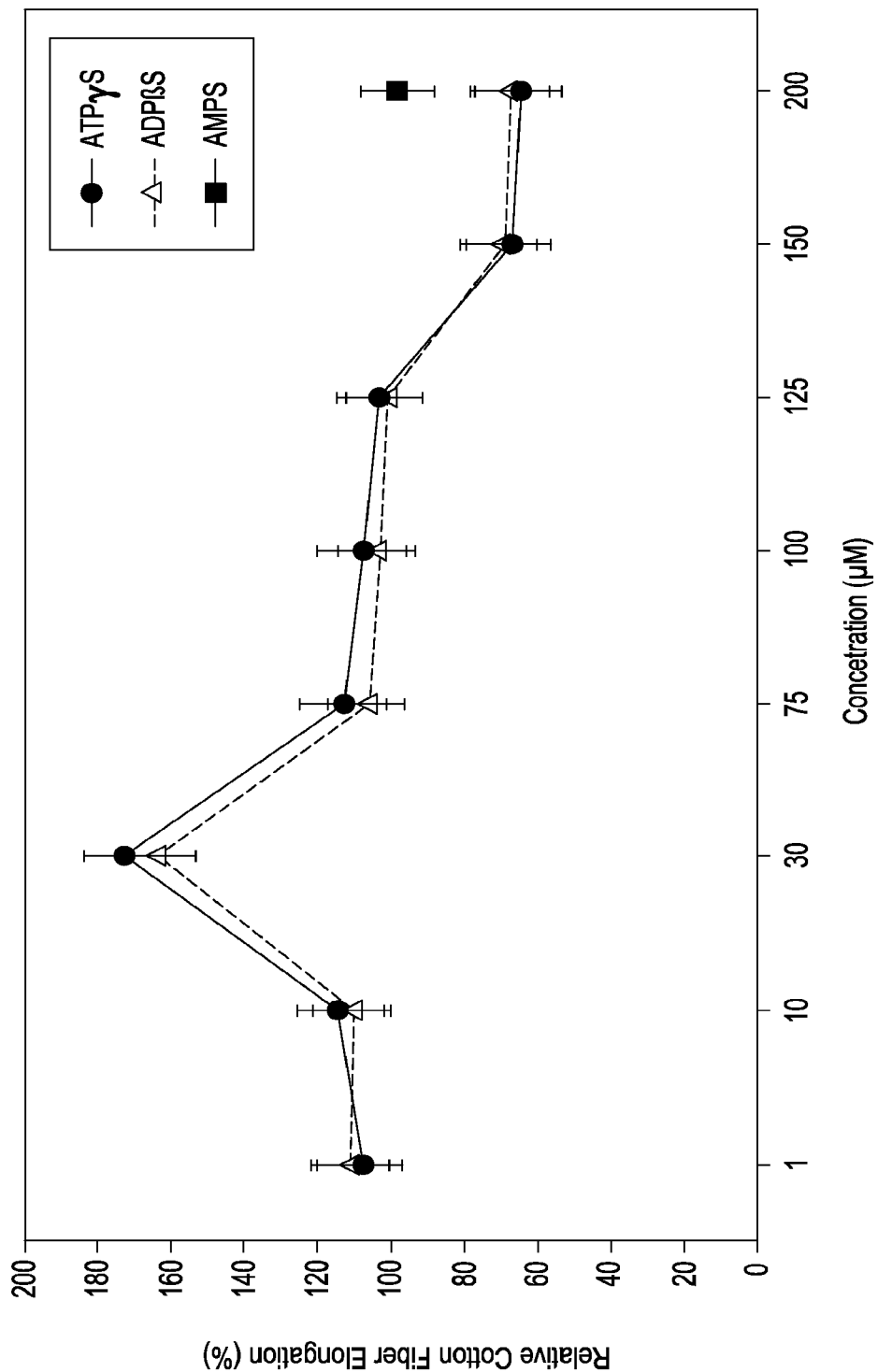
FIG. 6. Biphasic dose response curve for ATPγS and ADPβS.

Application of low levels of ATPγS and ADPβS promote fiber elongation. Representative images show that in the presence of 30 µM ATPγS and ADPβS cotton fibers grow noticeably longer by 7 dpa and that this promotion of growth can be blocked by the addition of PPADS and adenosine (FIG. 5A). Quantification of these growth changes indicate that these changes are statistically significant and that 30 µM ATPγS results in a 46% increase in average fiber length and 30 µM ADPβS causes a 44% increase in average fiber length (FIG. 5B). Also observed were statistically significant levels of promotion of cotton fiber growth at 5 dpa by 30 µM ATPγS and a statistically significant increase in the growth rate between 5 dpa and 7 dpa (data not shown). Application of both ATPγS and ADPβS results in a biphasic dose response curve for fiber growth with the threshold for promotion of growth somewhere between 10 and 30 µM and the threshold for inhibition of growth somewhere between 125 and 150 µM (FIG. 6). Application of AMPS, which cannot activate purinoceptors in animal cells, has no effect on fiber growth.

Genetic and biochemical approaches have been used to show that two ectoapyrases in Arabidopsis, AtAPY1 and AtAPY2 are critically needed for growth. For example, Arabidopsis double knockout mutants (apy1apy2) are severe dwarfs and inhibition of ectoapyrase activity with either chemical inhibitors or specific antibodies leads to inhibition of growth (Wolf et al., 2007; Wu et al., 2007). In addition the expression of these two apyrases is found in actively growing tissues (Wolf et al., 2007; Wu et al., 2007). Consistent with this result is the observation that higher levels of eATP are found in the extracellular matrix of actively growing tissues in *Medicago truncatula* (Kim et al., 2006). This correlation of apyrase expression and localization of eATP in growing cells suggests that it is important to regulate the eATP signal during growth. In this study we show that message levels of the cotton fiber apyrase GhAPY1, which has high sequence similarity to AtAPY1 and AtAPY2, is up-regulated during the rapid phase of fiber elongation.

Motif analysis indicates that GhApy1 contains a putative uncleavable signal peptide located near its N-terminus. This structure could anchor GhAPY1 to the membrane at its N-terminus and orient the protein domains responsible for enzyme activity out into the extracellular matrix, allowing it to function as an ectoapyrase like its close homologues AtAPY1 and AtAPY2. Consistent with this interpretation, suppression of fiber apyrase activity by selective inhibitors leads to an increase in the concentration of the eATP associated with growing cotton fibers. The two chemical apyrase inhibitors tested have been well characterized (Windsor et al, 2002; Windsor et al., 2003), and have been shown to inhibit pollen tube germination and elongation (Wu et al., 2007). They also inhibit fiber elongation in parallel with the rise in [eATP]. Both of these inhibitors are sufficiently hydrophobic to cross the plasma membrane and target apyrases inside the cell, and this could also affect fiber growth. However the chemical inhibitor effects are replicated by anti-apyrase antibodies, which are large proteins that are unlikely to cross the plasma membrane. Our finding that treatment of the growing fibers with anti-apyrase antibodies also resulted in inhibition of fiber growth and accumulation of eATP strongly supports the hypothesis that ectoapyrase activity is critical for fiber elongation. The antibodies and apyrase inhibitors would likely inhibit any ectoapyrase expressed in cotton fibers, and so, although GhAPY1 expression correlates closely with fiber growth, it may not be the only ectoapyrase that regulates cotton fiber growth.

The rise in [eATP] that results from suppressing ectoapyrase activity could be the signal that leads to the inhibition of fiber growth. This hypothesis is supported by our results showing that application of micromolar concentrations of poorly hydrolysable nucleotides can also inhibit fiber growth. Because cotton fiber elongation is regulated by micromolar [eATP] and because antagonists of animal purinoceptors block these growth responses, we predict that the metabolic pathway that links eATP to growth changes in cotton begins in plants as in animals with the binding of eATP to a plasma membrane receptor. Thus far the plant eATP receptor has not been found, but recently eATP receptors have been identification in the slime mold Dictyostelium and in the green algae (Fountain et al., 2007, 2008).

Results obtained in Arabidopsis thus far indicates the effects of eATP are transduced by an initial increase in the concentration of cytosolic calcium $[Ca^{2+}]_{cyt}$, followed by the activation of calcium-binding proteins. Two growth-affecting metabolic steps downstream of (and dependent on) the calcium signal in plants is an increased production of reactive oxygen species (ROS) and an increased production of ethylene. Recent results in cotton implicate ROS (Li et al., 2007) and ethylene (Shi et al., 2006) as key mediators of cotton fiber growth. In Arabidopsis genetically blocking ROS production blocks eATP effects on wound signaling, and blocking ethylene production blocks eATP effects on growth inhibition (Butterfield, 2007). Moreover, applied ATP induces ACC synthase expression in a calcium-dependent way (Jeter et al., 2004). We are currently testing whether eATP induced changes in cotton fiber elongation are linked to increased production of ROS and/or an increased production of ethylene in cotton fibers, both of which are dependent on extracellular calcium.

There are other hormone-mediated signaling pathways that could also be interacting with the eATP signal to regulate fiber growth. For example, apyrases and eATP have been implicated in the inhibition of the transport of the growth hormone, auxin (Tang et al., 2003). eATP has also been shown to promote the production of nitric oxide (NO) in tomato cell suspensions and during wound responses in the green algae, *Dasycladus vermicularis* (Foresi et al., 2007; Torres et al., in press). NO also appears to play an important role during plant growth (Pagnusat et al., 2004). It is interesting to find that eATP/apyrase signaling regulates growth in pollen tubes which grow via polar tip growth as well as cotton fibers which grow via diffuse growth as there arc clear cytological differences during these two types of growth (Tiwari and Wilkins, 1995). In both cases growth would be expected to be accompanied by fusion of secretory vesicles the possible release of ATP which could then act as a feedback signal to regulate growth. Genetic studies will be the next step toward further clarifying the precise function of GhApy1 and the role of extracellular nucleotide signaling during cotton fiber growth.

Plant Materials. Upland cotton (TM-1) was grown in a soil mixture in a fully automated green house. Flowers were picked and used for in vitro ovule culture studies. In studies using RNA extraction, 2- to 7-DPA ovules were harvested and immediately frozen using liquid nitrogen and then stored in a −80° C. refrigerator until they were analyzed.

Cloning of GhAPY1. Cotton EST TC59992, a putative apyrase full-length consensus sequence assembled from partial transcripts from several libraries (including *G. arboreum*, *G. raimondii*, and *G. hirsutum*) was generously supplied by Andrew Woodward in the C. Chen lab at the University of Texas. This sequence was used to design PCR primers with the following sequences: GhAPY1F (5'-ATGATCAAGCGTTCAATGGCG3') (SEQ ID NO.: 1) and GhAPY1R (5'CCTCATTGCTGATACAGCTTCGATGGC3')(SEQ ID NO.: 2), which were used to amplify RNA message from whole cotton leaf RNA. Cotton leaf RNA was isolated using the Sigma Spectrum Plant Total RNA Kit kit, and first-strand cDNA was synthesized using RT-PCR. This cDNA was used as template for Roche Expand Hi-Fidelity Taq DNA polymerase to amplify putative cotton apyrase. Amplified message was cloned into the expression vector pTrcHis2 using Invitrogen pTrcHis and pTrcHis2 TOPO TA Expression kit. The vector used in this kit adds both Myc and 6X-Histidine tags to the C-terminus of the cloned sequence. Invitrogen Top 10 chemically competent *E. coli* cells were then transformed with this construct. The sequence of the putative transformants were confirmed at the University of Texas ICMB Core DNA facility by sequencing with AB 3130 and AB 3730 DNA Analyzers.

Laser capture microdissection (LCM) and RNA preparation. For the young ovule tissues such as the ovules at −2 DPA, 0 DPA, and 2 DPA, laser capture microdissection and antisense RNA amplification were necessary because the fiber initials (or primordial cells in the epidermis) during fiber initiation are only a small portion of the ovule cells which makes technical difficulties on tissue preparation. Cotton ovules collected at −2 DPA, 0 DPA, and 2 DPA were fixed in a fixative (3:1 ethanol:acetic acid) for 10 min and vacuum infiltrated on ice for 20 min. The infiltrated tissues were incubated at 4° C. for 1 hour with rotation. The vacuum infiltration and incubation process were repeated twice with fresh fixative. Tissues infiltrated with 10 ml of 10% sucrose for 15 min, rotated overnight at 4° C. and repeated with 15% sucrose for cryoprotection. The fixed ovules were embedded with Tissue-Tek® Optimal Cutting Temperature (O.C.T.) (Sakura Finetek U.S.A., Torrance, Calif.) in cryo-mold. The embedded ovules were freezed immediately in liquid nitrogen and stored at −80° C.

Cryosectioning was performed with a Leica Cryostat (Leica Microsystems, Bannockburn, Ill.) in the microscopy facility at the University of Texas at Austin. The block was equilibrated at −20° C. for 1 hour and cryosectioned at 10 μm. The slides with cryosectioned ovules were dehydrated with a series of ethanol (70%, 95%, and 100%) form 2 min each on ice and transferred to histoclear (National Diagnostics, Atlanta, Ga.).

The PALM laser capture system (P.A.L.M. Microlaser Technologies AG Inc., Bernried, Germany) was used for laser capture microdissection. Individual fiber initials (−2 DPA and 0 DPA) or epidermal cells (2 DPA) were catapulted and then 45 μl of RNALater (Ambion, Austin, Tex.) was added. The antisense RNAs were processed from the captured cells using MessageAmp II aRNA amplification kit (Ambion, Austin, Tex.). Cotton ovules at 5 DPA and 7 DPA were processed with Spectrum Plant RNA kit (Sigma, St. Louis, Mo.) without laser capture microdissection.

Quantitative RT-PCR (qRT-PCR) analysis. First strand cDNA synthesis was performed using aRNA (for tissues at −2 DPA, 0 DPA, and 2 DPA) or total RNA (for tissues at 5 DPA and 7 DPA) and SuperScript II (Invitrogen, Carlsbad, Calif.). For the transcript amplification, gene-specific primers (Forward: 5'-ATC CAC AGG CTG CTG CAA AT-3' (SEQ ID NO.: 3), Reverse: 5'-AAT GCC CTC AGA CCA GCA GTT-3' (SEQ ID NO.: 4)) were designed using Primer Express version 2.0 software (Applied Biosystems, Foster City, Calif.). The qRT-PCR reaction was carried out in a final volume of 20 μl containing 10 μl SYBR Green PCR master mix (Applied Biosystems, Foster City, Calif.), 1 μM forward and reverse primers, and 0.1 μM cDNA probe in a ABI7500 Real-Time PCR system (Applied Biosystems, Foster City, Calif.). Cotton HISTONE3 (AF024716) was used to normalize the amount of gene-specific RT-PCR products (Wang et al., 2004). All reactions were performed in three replications and the amplification data were analyzed using ABI7500 SDS software (version 1.2.2) and the fold changes were calculated using the standard in each reaction.

Immunoblot analysis. At 0 and 7 DPA of in vitro ovule culture, cotton ovules were harvested and samples were placed in 1.5 ml centrifuge tubes then frozen with liquid nitrogen. Frozen samples were then ground at 4° C. using a micro mortar in the presence of a buffer containing 45 mM Tris, 150 mM NaCl, 1.2 mM EGTA, 5 mM DTT and protease inhibitors. Samples were then aliquoted for loading and boiled in the presence of SDS sample buffer for 3 min. After boiling, samples were centrifuged for 30 s at RT. Proteins were then separated via 10% SDS-PAGE, transferred to 0.45 nm nitrocellulose membranes (Schleicher & Schuell), and blocked for 2 hrs with 1% dry milk in PBS pH 7.5 (Blotto). The membrane was then incubated overnight at 4° C. with protein A-sepharose purified anti-Apy1 antibody diluted 1:250 with 1% Blotto. After three washes in 1% Blotto, the membrane was incubated for 1 hr at room temperature with affinity-purified anti-guinea pig IgG (goat) coupled to an 800-nm fluorochrome diluted 1:10,000 (Rockland IRDye 800CW). After three washes with Blotto, the fluorochrome signals were detected and analyzed using the Odyssey infrared imaging system (LI-COR Biosciences).

In Vitro Ovule Culture. Cotton bolls were harvested within 24 hours of flower opening, 1-DPA, and all petals bracts, and sepals were removed. All collected cotton bolls were used within 24 hours of original harvest. If the bolls were not used immediately they were stored in a 4° C. refrigerator until ready for use. For sterilization, bolls were dropped into an 85% ethanol solution for at least 30 seconds but not more than two minutes and then removed with forceps. The excess ethanol was shaken off and the boll was passed through a flame until the residual ethanol was burned off. Ovules were then excised and placed in 10 mL of BT Cotton Media cell culture (Caisson Laboratories, Inc., North Logan, Utah, USA)+5.0 µM IAA and 0.5 µM $GA_3$ (Sigma, St. Louis, Mo., USA) hormone solution, final concentration, in 60×15 mm Petri dishes and were then wrapped in Milli Wrap (Millipore Corporation, Bedford, Mass.). Twelve to 16 cotton ovules were placed into their respective Petri dishes and incubated with nucleotides, inhibitors, antibody serum or a combination of these at specified concentrations and were cultured at 32° C. in the dark without agitation. To facilitate combing of the cultured ovules, ovules were placed in a 75% ethanol solution for 15 minutes and then taken out to be combed. Fiber lengths were measured manually with a dissecting microscope after laying the ovule on its side and combing the fiber cells away from the ovule with forceps and dissecting probe.

In Vitro Cotton Ovule Culture Treatments. For studies testing the effects of apyrase inhibitors on cotton fiber growth, the inhibitors (NGXT191 and AI #4, both at 2.5 mg/mL), were dissolved in dimethyl sulfoxide and then applied to Cotton Media cell culture at 3 and 5 DPA after the introduction of cotton ovules to the media. For experiments testing the effects of apyrase antibodies on cotton fiber growth, apyrase antibodies were applied to Cotton Media cell culture at 3 and 5 DPA after the introduction of cotton ovules in the appropriate amounts. For experiments testing the effects of applying nucleotides during cotton fiber growth, various concentrations of ATPγS, ADPβS, and AMP (Sigma-Aldrich, Inc., St. Louis, Mo., USA) were added to Cotton Media cell culture at 5 DPA after the introduction of cotton ovules in the appropriate amounts. All nucleotides were made into 50 mM stocks dissolved in de-ionized water and kept at −20° C. while not in use. The inhibitor stocks were stored at −20° C. while not in use. For experiments testing the effects of P2-receptor antagonists, the antagonists (PPADS and Adenosine, stocks at 50 mM) were dissolved in de-ionized water and then applied to Cotton Media cell culture at 3 and 5 DPA for inhibitor and antibody experiments and 5 DPA for applied nucleotide experiments. The antagonists stocks were stored at ~20° C. while not in use (Sigma-Aldrich, Inc., St. Louis, Mo., USA). The ethylene inhibitor (S)-trans-2-Amino-4-(2-aminoethoxy)-3-butenoic acid hydrochloride (Sigma-Aldrich, Inc., St. Louis, Mo., USA) (AVG, stock at 50 mM) was dissolved in de-ionized water and then applied to Cotton Media cell culture at 5 DPA. The production of the Arabidopsis anti-APY1 and APY2 antibodies used is described by Steinebrunner et al. (2003). The crude immune and pre-immune sera were purified using protein A-sepharose following the protocol described by Martin et al. (1982) with the slight modification that the buffers used were azide-free. Bio-rad assay was used to determine that the concentration of the immune serum and pre-immune serum which was 0.46 µg/mL and 0.3 µg/mL, respectively.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Basra A S, Malik C P (1984) Development of the cotton fiber. Int. Rev. Cytol. 89: 65-113
Bendtsen J D, Nielsen H, von Heijne G, and Brunak S. (2004). Improved prediction of signal peptides: SignalP 3.0. J. Mol. Biol. 340, 783-795.
Chen Z J, Scheffler B E, Dennis E (2007) Toward Sequencing cotton (*Gossypium*) Genomes. Plant Physiol. 145: 1303-1310
Fountain S J, Parkinson K, Young M T, Cao L S, Thompson C R L, North R A (2007) An intracellular P2X receptor required for osmoregulation in Dictyostelium discoideum. Nature 448: 200-203
Gao P, Zhao P M, Wang J, Wang H Y, Wu X M, Xia G X (2007) Identification of genes preferentially expressed in cotton fibers: A possible role of calcium signaling in cotton fiber elongation. Plant Sci. 173: 61-69
Jeter C R, Tang W Q, Henaff E, Butterfield T, Roux S J (2004) Evidence of a novel cell signaling role for extracellular adenosine triphosphates and diphosphates in Arabidopsis. Plant Cell 16: 2652-2664
Kim H J, Triplett B A (2001) Cotton fiber growth in planta and in vitro. Models for plant cell elongation and cell wall biogenesis. Plant Physiol. 127: 1361-1366
Kim S Y, Sivaguru M, Stacey G (2006) Extracellular ATP in plants. Visualization, localization, and analysis of physiological significance in growth and signaling. Plant Physiology 142: 984-992
Lee J J, Woodward A W, Chen Z J (2007) Gene expression changes and early events in cotton fibre development. Annals Bot. 100: 1391-1401
Li H B, Qin Y M, Pang Y, Song W Q, Mei W Q, Zhu Y X (2007) A cotton ascorbate peroxidase is involved in hydrogen peroxide homeostasis during fibre cell development. New Phytol. 175: 462-471
Luo M, Xiao Y H, Li X B, Lu X F, Deng W, Li D, Hou L, Hu M Y, Li Y, Pei Y (2007) GhDET2, a steroid 5 alpha-reductase, plays an important role in cotton fiber cell initiation and elongation. Plant J. 51: 419-430
Martin L N. 1982. Separation of guinea pig IgG subclasses by affinity chromatography on protein A-Sepharose. Journal of Immunological Methods 52: 205-212
Panikashvili D, Savaldi-Goldstein S, Mandel T, Yifhar T, Franke R B, Hofer R, Schreiber L, Chory J, Aharoni A (2007) The Arabidopsis DESPERADO/AtWBC11 transporter is required for cutin and wax secretion. Plant Physiol. 145: 1345-1360
Roux S J, Song C, Jeter C (2006) Regulation of plant growth and development by extracellular nucleotides. In F Baluska, S Mancuso, D Volkmann, eds, Communication in Plants. Springer, Berlin, pp 221-234
Roux S J, Steinebrunner I (2007) Extracellular ATP: an unexpected role as a signaler in plants. Trends Plant Sci. 12: 522-527
Shi Y H, Zhu S W, Mao X Z, Feng J X, Qin Y M, Zhang L, Cheng J, Wei L P, Wang Z Y, Zhu Y X (2006) Transcriptome profiling, molecular biological, and physiological studies reveal a major role for ethylene in cotton fiber cell elongation. Plant Cell 18: 651-664
Taliercio E W, Boykin D (2007) Analysis of gene expression in cotton fiber initials. BMC Plant Biol. 7: 22
Tang W Q, Brady S R, Sun Y, Muday G K, Roux S J (2003) Extracellular ATP inhibits root gravitropism at concentrations that inhibit polar auxin transport Plant Physiol. 131: 147-154
Tiwari S C, Wilkins T A (1995) Cotton (*Gossypium-hirsutum*) Seed Trichomes Expand Via Diffuse Growing Mechanism. Canadian J. Botany 73: 746-757
Wilkins T A, Arpat A B (2005) The cotton fiber transcriptome. Physiologia Plantarum 124: 295-300
Windsor J B., Thomas C, Hurley L, Roux S J, Lloyd A M (2002) Automated colorimetric screen for apyrase inhibitors. Biotechniques 33: 1024-1030
Windsor B, Roux S J, Lloyd A (2003) Multiherbicide tolerance conferred by AtPgp1 and apyrase overexpression in Arabidopsis thaliana. Nature Biotechnology 21: 428-433
Wolf C, Hennig M, Romanovicz D, Steinebrunner I (2007) Developmental defects and seedling lethality in apyrase AtAPY1 and AtAPY2 double knockout mutants. Plant Mol. Biol. 64: 657-672
Wu J, Steinebrunner I, Sun Y, Butterfield T, Torres J, Arnold D, Gonzalez A, Jacob F, Reichler S, Roux S J (2007) Apyrases (nucleoside triphosphate-diphosphohydrolases) play a key role in growth control in Arabidopsis. Plant Physiol. 144: 961-975
Zhu Y Q, Xu K X, Luo B, Wang J W, Chen X Y (2003) An ATP-binding cassette transporter GhWBC1 from elongating cotton fibers. Plant Physiol. 133: 580-588

The invention claimed is:

1. A method of increasing plant fiber growth comprising: contacting a plant cell with one or more extracellular exogenous nucleotides selected from ATPγS and ADPβS at a concentration that increases growth of one or more cotton fibers, wherein said increasing results in an increase in cotton fiber growth as compared to a plant cell that lacks said contacting; and wherein:
the one or more extracellular nucleotides are provided at a concentration between 20 μM and 50 μM to increase the growth of the one or more cotton fibers.

2. The method of claim 1, wherein the one or more extracellular nucleotides are provided at a concentration of 30 μM.

3. The method of claim 1, wherein the one or more extracellular nucleotides comprises:
ATPγS; or
ADPβS.

* * * * *

UNITED STATES PATENT AND TRADEMARK OFFICE
CERTIFICATE OF CORRECTION

PATENT NO. : 11,555,200 B2
APPLICATION NO. : 16/405105
DATED : January 17, 2023
INVENTOR(S) : Stanley J. Roux et al.

It is certified that error appears in the above-identified patent and that said Letters Patent is hereby corrected as shown below:

On the Title Page

Item (60) delete "Provisional application No. 61/120,273 filed on Feb. 5, 2008", insert --Provisional application No. 61/120,273 filed on Dec. 5, 2008--

Signed and Sealed this
Twenty-first Day of November, 2023

Katherine Kelly Vidal
*Director of the United States Patent and Trademark Office*